United States Patent [19]

Geary, Sr.

[11] Patent Number: 4,828,602
[45] Date of Patent: May 9, 1989

[54] PLANT ANTITRANSPIRANT

[75] Inventor: Robert J. Geary, Sr., Vero Beach, Fla.

[73] Assignee: Saint Thomas Fund, Vero Beach, Fla.

[21] Appl. No.: 170,860

[22] Filed: Mar. 21, 1988

[51] Int. Cl.$^4$ .............................................. A01D 43/04
[52] U.S. Cl. .................................................... 71/85
[58] Field of Search ............................................ 71/85

[56] References Cited
U.S. PATENT DOCUMENTS
4,618,442 10/1986 Geary, Sr. .............................. 252/70

Primary Examiner—Catherine L. Mills
Attorney, Agent, or Firm—Samson B. Leavitt; Michael A. Leavitt

[57] ABSTRACT

A method is disclosed for increasing the resistance of plants to damage by non-freezing dehydrating conditions comprising treating the plants with an aqueous medium containing a nonionic surface active polyethoxylated polyoxypropylene block copolymer of about 2,000 to 9,000 average molecular weight, and optionally urea and/or a UV absorber, and/or finely ground, readily dispersible zinc oxide, aluminum oxide or titanium dioxide reflecting agent, and compositions for use in such method.

8 Claims, No Drawings

PLANT ANTITRANSPIRANT

This invention relates to plant antitranspirant compositions and methods for their use, i.e. for increasing the resistance of plants to undue transpiration (loss of water, desiccation, dehydration) and damage caused by drought, sun, wind, failure to timely water or irrigate, and other non-freezing dehydrating conditions.

Such dehydrating conditions have always been a major cause of temporary or permanent damage to substantially all types of plants and plant parts which almost without exception require a continuous and/or regular supply of water to remain alive and grow. Many antitranspirants developed heretofore depend upon a thorough coverage of the upper and lower surfaces of the plant leaf to prevent moisture from escaping from the leaf and plant (transpiration). Treating, e.g. spraying of the plant with a suitable systemic antitranspirant chemical prior to exposure to dehydrating conditions would appear to constitute a simple and relatively inexpensive solution to the problem. However, despite many attempts to find and provide such a chemical, no really effective, practical and commercially acceptable methods have resulted to date, due to side effects, unduly low activity, etc.

It is an object of this invention to provide such a chemical. Another object of this invention is the provision of a plant antitranspirant chemical which will not be subject to one or more of the above disadvantages. Still another object of this invention is the provision of such a plant chemical which is nonphytotoxic, nontoxic, biodegradable and environmentally acceptable. Yet another object of this invention is the provision of compositions and methods for employing such chemical for antitranspiration, i.e. increasing the resistance of plants to damage by dehydrating conditions. Other objects and advantages will appear as the description proceeds.

In U.S. Pat. No. 4,618,442 issued Oct. 21, 1986 to the present applicant and Robert J. Geary III there are disclosed and claimed methods and compositions for plant cryoprotection, i.e. increasing the resistance of the plants to freezing temperatures, involving the use of nonionic surface active polyoxyethylenated polyoxypropylene block copolymers. I have now found that these same copolymers are effective antitranspirants which when applied to the plant leaf, are absorbed in a few hours into and/or between the cells of the leaf where they, by a mechanism not yet fully understood, act to prevent undue transpiration, i.e. evaporation of water/moisture from the leaf except as necessary for normal growth.

Accordingly, the attainment of one or more of the above objects is made possible by this invention which includes the provision of a method of increasing the resistance of plants to damage by non-freezing dehydration conditions comprising applying to the plant surface at ambient non-freezing temperatures prior to significant damage by, and up to about 30 days prior to exposure to, such conditions an aqueous liquid containing, approximately by weight and as an essential active antitranspirant, 0.02% to 2.5% of one or a mixture of nonionic surface active polyethoxylated polyoxypropylene block copolymers having an average molecular weight of about 2,000 to about 9,000 and a weight ratio of propylene oxide:ethylene oxide of about 9:1 to about 0.7:1.

The invention further includes the provision of an aqueous plant antitranspirant composition containing approximately by weight and as essential antitranspirant components, 0.02% to 2.5% of one or a mixture of nonionic surface active polyethoxylated polyoxypropylene block copolymers having an average molecular weight of about 2,000 to about 9,000 and a weight ratio of propylene oxide: ethylene oxide of about 9:1 to about 0.7:1, and about 0.5 to about 2 parts of urea per part of said copolymers. The invention also includes the method of treating plants with the aforesaid composition. Optionally, the invention also includes the use of compositions also containing about 25 to about 2,000 ppm of a UV absorber based on the weight of the copolymers therein.

Subject to modifications discussed below, the descriptions of operative block copolymers, concentrations, prescribed and proscribed materials, conditions and methods, and suitable apparatus described in the passage from column 2, line 15 to column 4, line 23 of the aforesaid U.S. Pat. No. 4,618,442 are applicable and such passage is accordingly incorporated herein by reference thereto.

Generally, block copolymers of lower molecular weight (M.W.) in the range of about 2000 to 45000 or 6500 are preferred, with lower ethylene oxide (E.O.) content of about 10% to 20% or 30%. Such copolymers of higher polyoxypropylene (Pr.O) content are poorly soluble to insoluble in water, which tends to prevent removal of these compositions from the plant surfaces by rain, spraying or irrigation, and to expedite and increase the absorption of the compositions into the plant. Mixtures of such copolymers can be used having the desired average M.W., including for example mixing a liquid copolymer (Pluronic L series) with a pasty copolymer (Pluronic P series) or prilled copolymer (Pluronic F series). All these block copolymers can be supplied and used in 100% form without solvents, or as a concentrate of from about 20 or 50 to 99% in water or an organic solvent such as a water miscible polyhydric alcohol (glycerin, propylene glycol, etc.), a 1:1 mixture of ethyl acetate and methanol, etc. Insoluble copolymers cold with vigorous agitation, be emulsified in water to form water-in-oil or oil-in-water emulsions.

Potassium and/or sodium ion content of over 27 ppm in the instant compositions inhibit antitranspirancy and shoulder therefore be avoided.

The compositions of this invention can be applied in any desired manner, e.g., spraying, dipping, irrigating, root feeding, etc., to any and/or all plant surfaces, i.e. leaf, stem, bark, root, flower, bud, fruit, etc. up to about 30 days, preferably about 6 or 8 to about 24 hours, prior to exposure to dehydrating conditions. Repeated treatment a few days apart is often highly effective in building up the desired antitranspirant property in the plant which may be of any type, size and stage of growth.

According to a further feature of this invention, further improved antitranspirancy and recovery after exposure to dehydrating conditions are obtained by including in the instant compositions about 25 to about 2,000 ppm, based on the weight of the copolymer of one or any mixture of UV stabilizers (UV absorbers, anti-UV agents, etc.). Such UV stabilizers are well known in the art, and illustratively but not limitatively may comprise 2-hydroxybenzophenones, benzotriazoles having a 2-(2-hydroxyphenyl) group, esters, tri-aryltriazines in which at least one aryl group has an o-hydroxy substituent, benzothiazoles, benzylidene-malonic esters, arylaminoethylenes and 1,2-dibenzoyl-3-aryl guanidines and the like as disclosed in column 5, line 67 to column 6, line 37 of U.S. Pat. No. 3,429,732 to Baitinger, which passage is herein incorporated by reference thereto. Preferred as the oxalanilide and especially fluorescein and the benzophenone and benzotriazole type UV stabilizers.

According to a still further feature of this invention, more improved antitranspirancy properties and recovery after exposure to dehydrating conditions are obtained by including in the instant compositions about 0.5 to about 10%, preferably about 1 to about 6%, of one or any mixture of finely ground, readily dispersible reflecting agents selected from the group consisting of aluminum oxide, titanium dioxide, and preferably zinc oxide. The term "readily dispersible" refers to the ability of the agent to form a substantially stable suspension in the instant aqueous compositions, i.e. to resist settling out for at least about 30 minutes, more preferably at least a day, still more preferably up to about three months or indefinitely in storage. It is believed that the reflecting agent achieves these improved results by reducing the temperature of the exposed plant parts such as the leaves on sunny days. This agent may be employed instead of or in addition to the above-described urea and/or UV stabilizer additives, and is preferably mixed into the composition after the described nonionic block copolymer to promote and expedite its dispersion.

EXAMPLE 1

Following are some typical exemplary instructions to the consumer for using the antitranspirant compositions and methods of this invention, employing a solution concentrate of ⅓ copolymer of 4500 M.W., Pr.O:E.O. of 1:1, ⅓ copolymer of 2000 M.W., Pr.O:E.O of 9:1, ⅓ propylene glycol (exempt from tolerances on foods by EPA No. 40 CFR 180.1001 (c) and (e).

Recommended procedure is to spray the plants while they are still turgid and not suffering from dehydration by sun or wind. Ordinary sprayers can be used and the dilution rate should be 1 oz. concentrate to 4 gal. water or approx. 10 cc. to 1 gallon. The plant should not be watered overhead for at least 8 hours. If rain occurs during this time, it is desirable to respray the plants.

Before transplanting, the tops of the plants can be dipped in a ½ dose of the spray solution concentrate of 1 oz. to 8 gallons of water or 5 cc. to a gallon of water. Soaking the roots of the plants should be avoided as much as possible.

For citrus trees, it is recommended that 2 sprayings of 2 pints concentration to 100 gallons be applied spacing the application if possible a week apart, the last one being applied immediately before transplant. Normal water procedures and heavy watering of the roots is recommended.

On grasses of lawns and fairways, spray as soon as possible after mowing and watering and repeat the spraying after the next mowing.

For cuttings of plants that are to be rooted, spray the plants twice, a week apart, before cutting them from the plant. On plants that lose latex, scorch the ends of the cuttings to coagulate the latex, dip the ends of the cuttings in rooting substances containing Indole Butyric Acid or Napthalene Acetic Acid. Firm in sand or rooting media firmly around the cuttings.

The following further examples of certain embodiments of this invention are to be regarded as only illustrative and not limiting. All amounts and proportions referred to herein and in the appended claims are by weight, and temperatures are in degrees F. unless otherwise indicated.

| Example | Copolymer M.W. | Copolymer Pr.O.:E.O. | Copolymer:Solvent |
|---|---|---|---|
| 2 | 4,500 | 1:1 | 1:1 propylene glycol |
| 3 | 8,350 | 4:1 | 1:1 ethyl acetate:methanol |
| 4 | 7,700 | 4:1 | acetate:methanol |
| 5 | 3,650 | 4:1 | 1:0 |
| 6 | 2,650 | 7:3 | 1:0 |
| 7 | 2,000 | 9:1 | as in Example 3,4 |

EXAMPLE 8

Plants of the species Snapdragons, Petunias, Tomatoes, Peppers, Crown of Thorns, Gardenias, Hibiscus, Blue Daisy and Strawberries in good growing condition, some flowering, with nursery soil around the roots, are planted in the field in very sandy, poor soil and watered thoroughly with overhead sprinklers daily for a week. All except control plants are then sprayed twice, a week apart, with aqueous compositions containing varying concentrations ranging from about 0.025 to about 0.5 wt. % of each of the concentrates of Examples 1-7, with similar compositions also containing varying concentrations ranging from about 0.5 to about 2 parts of urea per part of the copolymer, with similar compositions further containing varying concentration ranging from about 25 to 2,000 ppm of fluorescein based on the weight of the copolymer, and with similar compositions further containing varying concentrations in the range of about 0.5 to about 10% of zinc oxide, aluminum oxide and/or titanium dioxide. On other days in between they are all watered. After the second treatment with the antitranspirant composition they are not watered for 10 weeks with temperatures ranging from the high 80's daytime to the 50's nighttime. During this time the untreated control plants wither and die while the treated plants exhibit normal growth during the first month and survive, though not all with good vigorous growth, after the 10 week drought. These tests indicate that plants treated in accordance with this invention can survive under desert conditions or where wind blasts and other dehydrating factors are present which normally would kill the plants.

EXAMPLE 9

Plants of leucanthemum (chrysanthemum), tomatoes, roses and poinsettias are all, except for control plants, sprayed 2 times at an interval of a week with antitranspirant compositions as employed in Example 8 to permit the plants to absorb and assimilate the copolymers. Tip cuttings are made and cuttings inserted into coarse sand washed free of excess salt. The poinsettia cuttings are first scorched with flame to prevent bleeding of the latex prior to insertion. The planted cuttings are placed in a shady cold spot without watering except the tomatoes and chyrsantheniums at insertion, roots of which emerge in 1 to 2 weeks. Roots of poinsettias and roses take up to a month to emerge. Control plats do not develop roots, and die.

EXAMPLE 10

Newly emerged seedlings of the monocotyledon grains corn, barley, wheat and rye in poor sandy soil are all, except for control plants, sprayed with light mists of antitranspirant composition as described in Example 8. One week later, and again at 2 weeks and 3 weeks, the sprayings are repeated at the same dosages but using a heavier spray. One day after the last treatment they are heavily watered and then left unwatered for about 1 month in which temperatures are unusually severe, ranging from over 80° F. and only 3 cloudy days daytime, and 74° to 76° F. nighttime. After the first week, the soil tests at only 50% moisture. This gradually drops to only 20% moisture at the end of the month. After the 1 month drought the plants are watered to continue growth. The corn plants are severely damaged, but the other plants, though somewhat inhibited in growth, produce grain. Control plants do not survive the drought.

EXAMPLE 11

Newly sprouted seedlings of the dicotyledons soybeans, string beans and black eye peas are, after the first true leaves appear, sprayed (except the control plants) with the antitranspirant compositions as described in Example 8 three times at 5 day intervals, with daily watering in between. Watering is then discontinued for 15 days during which the soil moisture drops to 50%. Thereafter, sufficient watering is resumed and beam and pea yields are obtained. Control plants do not survive.

This invention has been disclosed with respect to preferred embodiments, and it will be understood that various modifications and variations thereof obvious to those skilled in the art are to be included within the spirit and purview of this application and the scope of the appended claims.

What is claimed is:

1. A method of increasing the resistance of plants to damage by non-freezing dehydrating conditions comprising applying to the plant surfaces at ambient non-freezing temperatures prior to significant damage by, and up to about 30 days prior to exposure to, such conditions an aqueous liquid containing, approximately by weight and as an essential active antitranspirant, 0.02% to 2.5% of one or a mixture of nonionic surface active polyethoxylated polyoxypropylene block copolymers having an average molecular weight of about 2,000 to about 9,000 and a weight ratio of propylene oxide:ethylene oxide of about 9:1 to about 0.7:1.

2. A method according to claim 1 wherein said liquid contains about 0.02% to about 0.5 wt. % of said copolymers.

3. A method according to claim 1 wherein said copolymers have an average molecular weight of about 2,000 to about 6,500 and said weight ratio is about 4:1 to about 1:1.

4. A method according to claim 1 wherein said liquid further contains about 0.5 to about 2 parts of urea per part by weight of said copolymers.

5. A method according to claim 1 wherein said liquid further contains about 25 to about 2,000 ppm of a UV absorber based on the weight of said copolymers.

6. A method according to claim 1 wherein said liquid further contains about 0.5 to about 10 wt. % of one or any mixture of finely ground, readily dispersible reflecting agents selected from the group consisting of zinc oxide, aluminum oxide and titanium dioxide.

7. A method according to claim 4 wherein said liquid further contains about 25 to about 2,000 ppm of a UV absorber based on the weight of said copolymers.

8. A method according to claim 7 wherein said liquid further contains about 0.5 to about 10 wt. % of one or any mixture of finely ground, readily dispersible reflecting agents selected from the group consisting of zinc oxide, aluminum oxide and titanium dioxide.

* * * * *